United States Patent [19]

Kathawala

[11] 4,287,355

[45] Sep. 1, 1981

[54] CARBOXYL-(PHENYL OR TOLYL)-SULFONIUM SALTS

[75] Inventor: Faizulla G. Kathawala, Mountain Lakes, N.J.

[73] Assignee: Sandoz, Inc., E. Hanover, N.J.

[21] Appl. No.: 170,569

[22] Filed: Jul. 21, 1980

Related U.S. Application Data

[63] Continuation-in-part of Ser. No. 88,826, Oct. 26, 1979, abandoned, which is a continuation-in-part of Ser. No. 929,424, Jul. 31, 1978, abandoned.

[51] Int. Cl.$^3$ ............... A01N 9/12; A61K 31/235
[52] U.S. Cl. ............................ 560/18; 424/308; 424/317; 562/465
[58] Field of Search ............... 560/18, 9; 562/465; 424/308, 317

[56] References Cited

U.S. PATENT DOCUMENTS 3,600,437  8/1971  Marshall ........................... 260/520

OTHER PUBLICATIONS

Tsugio, et al. "Chemical Abstract" vol. 70, p. 28546b (1969).

*Primary Examiner*—Werren B. Lone
*Attorney, Agent, or Firm*—Gerald D. Sharkin; Richard E. Vila; Frederick H. Weinfeldt

[57] ABSTRACT

Carbalkoxy-phenyl (or tolyl)-dialkyl-or alkyl-phenyl-sulfonium salts, e.g. p-(α-carbethoxy) tolyl-n-octadecyl-phenyl sulfonium tetrafluoroborate, are useful as pharmaceuticals. The compounds are obtainable by reaction of a carbalkoxy-phenyl (or-tolyl)-dialkyl-or-alkyl-phenyl-sulfide with an alkylhalide in the presence of a metal salt, e.g. silver tetrafluoroborate.

27 Claims, No Drawings

CARBOXYL-(PHENYL OR TOLYL)-SULFONIUM SALTS

This is a continuation-in-part of copending application Ser. No. 88,826 filed Oct. 26, 1979, abandoned, which in turn is a continuation-in-part of then copending application Ser. No. 929,424 filed July 31, 1978 (now abandoned).

The invention relates to organic compounds, particularly carbalkoxy-phenyl (or tolyl)-dialyl-or-alkyl-phenyl-sulfonium salts, as well as to their use as pharmaceutical agents and pharmaceutical compositions containing such compounds.

The compounds of this invention may be conveniently represented by the formula I:

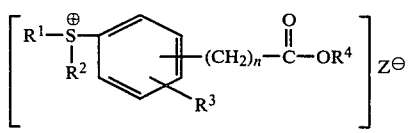

wherein:
- $R^1$ is alkyl having from 8 to 24 carbon atoms, (preferably from 10 to 20 carbon atoms);
- $R^2$ is alkyl having from 1 to 6 carbon atoms or unsubstituted or substituted phenyl of the formula:

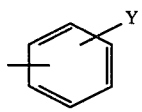

wherein
- Y is a hydrogen atom, fluoro, chloro or bromo, ie halo having an atomic weight of from about 19 to 80, alkyl of from 1 to 4 carbon atoms, or alkoxy of from 1 to 4 carbon atoms;
- $R^3$ is a hydrogen atom, fluoro, chloro or bromo, ie halo having an atomic weight of from about 19 to 80, alkyl having from 1 to 3 carbon atoms or alkoxy having from 1 to 3 carbon atoms;
- $R^4$ is a hydrogen atom, or alkyl having from 1 to 6 carbon atoms, (preferably ethyl);
- n is 0 or 1; and
- $Z^\ominus$ is an anion forming a pharmaceutically acceptable non-toxic salt of the corresponding cation; provided that $R^4$ is alkyl when $R^2$ is other than alkyl.

Preferred compounds of the invention have one and preferably more or all of the following features: (a) $R^1$ having 10 to 20 carbon atoms, more preferably 12 to 18 carbon atoms; (b) $R^2$ being alkyl or unsubstituted phenyl (Y being hydrogen), more preferably alkyl; (c) $R^3$ being hydrogen; (d) the carbalkoxy moiety being ortho or para to the sulfonium ion on the phenyl ring to which both are attached; and (e) $R^4$ is alkyl, more preferably ethyl. Subgroups within the scope of compounds I also include those in which n is 0 and those in which n is 1; the former being preferred.

Compounds Ia, ie compounds I, in which $R^{4'}$ is the same as $R^4$ as defined above when it is alkyl, may be prepared by reacting (Process A) a compound of the formula II:

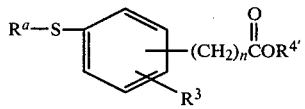

wherein n, and $R^{4'}$ are as above defined, and $R^a$ is either $R^1$ or $R^2$, as defined above, with an alkyl halide of the formula III:

$$X-R^b$$

wherein X is bromo or iodo, and $R^b$ is either $R^1$ when $R^a$ is $R^2$; or is $R^{2'}$ ie the same as $R^2$ when it is alkyl as defined above, when $R^a$ is $R^1$, in an inert solvent in the presence of a salt of the formula IV:

$$MZ \qquad\qquad IV$$

wherein Z is as above defined (for $Z^\ominus$), and M is a metal forming with X a salt MX which is either per se insoluble or relatively less soluble than the compound IV in the inert solvent.

Process (A) is carried out under essentially anhydrous conditions at moderate temperatures, eg. from 15° C. to 40° C., in an inert solvent eg. nitromethane or toluene. The reactants II and III are conveniently mixed in the solvent and the salt of the formula IV may be added thereto exercising suitable caution as may be required such as shielding from light. The reaction is also preferably carried out under an inert atmosphere, eg. dry nitrogen. An excess of the alkylhalide of the formula III is preferably employed and in most cases is highly desirable in order to increase the yield of the desired products. Illustrative of various MZ salts include the salts of noble metals of which silver represents a preferred metal. Other such metals include mercury. Representative anions ($Z^\ominus$) forming such salts include the tetrafluoroborate, trifluoromethylsulfonate and perchlorate ions. Other anions which may be represented by Z include the alkyl and phenyl sulfonates, eg. methanesulfonate, phenylsulfonate and p-toluenesulfonate. Examples of preferred salts of the formula IV include silver tetrafluoroborate and silver trifluoromethylsulfonate of which silver tetrafluoroborate is especially preferred. The resulting solvent insoluble salt, MX, is separated by known techniques and the desired product recovered from the solvent phase by applying conventional procedures to be selected in large part on the nature of the compound I being produced and the complexity of the remaining solvent reaction medium. It will be appreciated that where a Compound Ia is desired in which $R^2$ is other than alkyl, then a compound II is used in which $R^a=$such $R^2$ radical (not alkyl) and $R^b$ (of III) is $R^1$.

Compounds I in which $R^4$ is hydrogen and Z is $BF_4$, ie Compounds Ib may be obtained by adapting the procedure described in CA 70, 28546b for preparing lower analogs of the compounds of this invention (process B). Process (B) involves reacting an alkylthio aromatic acid of the formula II'

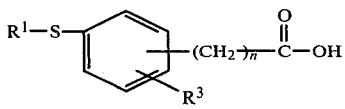 II' in which $R^1$, $R^3$, and n are as defined above, with a trialkyl oxonium tetrafluoroborate of the formula III'

 III' in which $R^{2'}$ is as defined above, in equivalent amounts, in an inert solvent, eg $CH_2Cl_2$, at moderate temperatures, eg room temperature. However, if an excess of the oxonium compound (III'), is used, the corresponding compound Ia is obtained in which $R^{2'}$ and $R^{4'}$ are both the same alkyl radical, as contributed by III'.

In other preparative procedures that may be defined as ion exchange reactions (generally herein designated process C), the compounds of the formula I may be converted into other salt forms.

For example, in a procedure herein designated process C-1, a compound of the formula I':

 I' may be converted into a compound of the formula I":

 I"

with K in formulae I' and I" representing the cation:

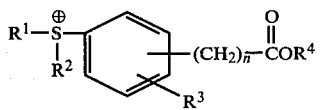

in which n, $R^1$, $R^2$, $R^3$ and $R^4$ are as defined above and wherein $Z_b^\ominus$ is an anion forming a compound I having different solubility characteristics than formed with the anion $Z_a^\ominus$. Conversely, the anion $Z_a^\ominus$ is anion forming a compound I having different solubility characteristics than is formed with the anion $Z_b^\ominus$.

More particularly, the compounds of the formula I" may be prepared in process C-1 by heating a compound I' in aqueous cosolvent solution in the presence of an acid of the formula V:

$$H-Z_b \quad \quad V$$

wherein $Z_b$ is as above defined, at temperatures typically of from about 55° C. to 120° C., preferably 65° C. to 100° C., desirably in the presence of a theoretical excess of the acid of the formula V, and separating the desired compound of the formula I" from any unreacted starting material by taking advantage of its different solubility characteristics.

Preferred compounds of the formula I' include those in which $Z_a^\ominus$ is the tetrafluoroborate ion. The aqueous cosolvent system comprises water and a sufficient amount of a water soluble organic solvent that the resulting aqueous cosolvent system is capable of dissolving the starting compound of the formula I'. Examples of such organic solvents include the lower alkanols, eg. methanol, ethanol and propanol, dimethylacetamide and dimethylformamide, particularly ethanol.

The initial isolation of the desired compound I" in process C-1 may be effected by the application of various known procedures depending upon the solubility characteristics of the desired product and any remaining unreacted starting material, as would be apparent to those skilled in the art. For example, isolation may be readily effected in certain cases simply by lowering the temperature of the reaction to crystallize the desired product by taking advantage of its reduced solubility in the aqueous cosolvent system. In other cases the contents of the reaction mixture may be concentrated and redissolved in a solvent from which either the desired product or undesired starting material may be selectively crystallized. In still other cases the contents of the reaction mixture may be subjected to standard chromatography procedures or subjected to the action of ion exchange resins.

Another ion exchange procedure that is particularly convenient (and is herein designated process C-2) involves generally the reaction of a compound I'''.

 I''' with a compound of the VI:

 VI in an aqueous cosolvent solution to obtain a compound of the formula $I^{iv}$:

 $I^{iv}$ with K in formulae I''' and $I^{iv}$ being as above defined, and wherein $M_a$ is a metal cation forming with the anion $Z_c^\ominus$ a salt $M_aZ_c$ that is less soluble in the cosolvent solution than the compound $I^{iv}$, $Z_d$ is an anion forming with $M_a$ the cosolvent soluble salt VI that is more soluble than $M_aZ_c$ and $Z_c^\ominus$ is conversely an anion forming with $M_a$ the salt $M_aZ_c$.

The process C-2 is more particularly carried out in an aqueous solution at temperatures preferably in the range of 50° C. to 120° C., more preferably 80° C. to 100° C., preferably with a theoretical excess of the compound V. The aqueous cosolvent employed is composed similarly to that used in process C-1 with ethanol being commonly preferred as the organic component of such solvent system.

By way of illustration, a preferred embodiment of process C-2 involves the use of a compound I''' in which $Z_c^\ominus$ is the tetrafluoroborate anion and $M_a$ is potassium whereby the insoluble potassium tetrafluoroborate is formed as a result of the reaction and may be separated from the reaction mixture by taking advantage of its insolubility in the aqueous cosolvent system. In such embodiment the desired compound of the formula $I^{iv}$ remains in the reaction system cosolvent and may be initially separated from any remaining undesired reactants and starting materials by employing conventional and well known procedures as in process C-1.

Other known ion exchange procedures such as those involving ion exchange resins may be employed, especially when representing a convenient method of separating desired products from reactants and starting materials in those procedures specifically detailed above, eg. processes C-1 and C-2. Typical ion exchange resins for such use are well known and are represented, for example, by the product obtainable under the trademark Dowex 1-X8. In effecting the initial isolation of the desired products from ion exchange reactions such as processes B-1 and B-2 by chromatographic procedures both thin layer and column chromatography may of course be employed. Typical chromatography additives for such use are well known and are represented, for example, by silica gel and by the products obtainable under the trademarks Amberlite XAD-2 and Sephadex LH20.

Various other ways of employing ion exchange procedures, such as those specifically detailed above, will be recognized by those skilled in the art. For example, procedures such as processes C-1 and C-2, above, may be combined with process (a), above, as the final stages thereof, in order to obtain the ultimately desired compound I from an intermediary compound I without effecting an actual recovery of the latter.

Final recovery of the desired compound of the formula I from ion exchange procedures such as processes C-1 and C-2 may be also effected by conventional techniques such as crystallization, precipitation, vacuum distillation and the like.

Starting materials and reagents used in the above-described reactions, e.g., compounds II, II', III, III', IV and V are either known and obtained by methods described in the literature, or where not known, may be obtained by methods analogous to those described in the literature.

The compounds I are useful for inhibiting and retarding the passage of glucose into the blood of mammals and therefore are particularly indicated as useful for treating obesity by the inhibition of such passage of glucose and as agents for inhibiting hyperglycemia, ie. as anti-hyperglycemic agents, by inhibiting or retarding such passage of glucose, particularly for inhibiting post-prandial hyperglycemia including desirably the inhibiting of post-prandial hyperglycemia in diabetic subjects. Such effect on the passage of glucose into the blood in mammals may be indicated by the glucose transport test in which male Wister rats are dosed orally with 0.3–80 mg./kg. body weight of the test compound after at least 20 hours of fasting. One hour after receiving the drug, each animal is sacrificed and the upper small intestine is removed and washed with glucose-saline. A 5 cm. section of the intestine is everted so that the mucosal surface is on the outside. One end of the segment is tied and the center of the sac so formed is filled with oxygen saturated Kreb's bicarbonate buffer. The other end is then closed to form a sac which is then incubated in 10 ml. of oxygen saturated bicarbonate buffer for 60 minutes at 37° C. Both the outside and inside solutions contain initially 0.3% of glucose. At the end of the incubation time, the glucose content of the outer (mucosal) and the inner (serosal) solution is determined using the standard Auto Analyzer procedure. Similar tests are run simultaneously with control animals receiving only the vehicle. The percent inhibition of glucose transport caused by the drug is calculated from the formula:

$$I = 100 - \left( \frac{S_t - M_t}{S_c - M_c} \times 100 \right),$$

wherein
I = percent inhibition,
$S_t$ = glucose concentration (mg.%) of serosal fluid at the end of an experiment in the drug-treated animal,
$S_c$ = glucose concentration (mg.%) of serosal fluid at the end of an experiment in the control animal,
$M_t$ = glucose concentration (mg.%) of mucosal fluid at the end of an experiment in the drug-treated animal, and
$M_c$ = glucose concentration (mg.%) of mucosal fluid at the end of an experiment in the control animal.

The precise dosage of the compound of Formula I to be employed depends upon several factors including the condition being treated, the severity of the condition, the result desired and the particular compound employed. However, in general, satisfactory results, eg. in the treatment of obesity, are obtained when a compound of Formula I is administered orally at a daily dosage of about 1–800 mg./kg. body weight, eg. a dosage of about 60–3600 mg, for most larger mammals. Usually, a small dosage is administered initially and the dosage is gradually increased until the optimal dosage for the host under treatment is determined. The unit dosages may be divided into two to four equal portions, or placed in sustained release form. A typical dosage for larger mammals is from about 15 to 1200 mg., eg from about 25 to 1000 mg., for administration desirably at meal time as conventional in treatments with substances having such activity, eg. three times a day, particularly before a carbohydrate-rich meal.

The compounds of Formula I may be formulated into conventional pharmaceutical compositions for oral administration.

The compounds may be combined with pharmaceutically acceptable carriers and other conventional pharmaceutical adjuvants and administered orally in the form of tablets, dispersible powders, granules, capsules, elixirs, suspensions and the like. The compositions may be prepared by conventional means and may contain one or more conventional adjuvants such as sweetening agents, other flavoring agents, coloring agents and preserving agents.

Tablets may contain the active ingredient in admixture with conventional excipients, i.e., inert diluents such as calcium carbonate, sodium carbonate, lactose, talc and sodium citrate, granulating and disintegrating agents, e.g., starch, gum tragacanth and alginic acid and also certain complex silicates, binding agents, e.g., starch, gelatin and acacia, and lubricating agents, e.g., magnesium stearate, stearic acid, talc and sodium lauryl sulfate. The tablets may be uncoated or coated by known techniques to delay disintegration and absorption in the gastrointestinal tract and thereby provide a sustained action over a longer period.

Capsules may contain a compound of Formula I alone but preferably admixed with an inert solid diluent, e.g., calcium carbonate, calcium phosphate, kaolin, lactose and high molecular weight polyethylene glycols.

Suspensions, syrups and elixirs may contain a compound of Formula I in admixture with any of the conventional excipients utilized for the preparation of such compositions i.e., suspending agents, e.g., methylcellulose, tragacanth and sodium alginate, wetting agents, e.g., lecithin, polyoxyethylene stearate and polyoxyethylene sorbitan monooleate, preservatives, e.g., ethyl p-hydroxybenzoate, and diluents, e.g., ethanol, propylene glycol and glycerin.

The preferred pharmaceutical compositions from the stand-point of ease of preparation and administration are solid compositions, particularly tablets and hard-filled capsules.

A representative formulation for administration orally three times a day prior to feeding in the treatment or lessening of obesity in larger mammals is a gelatin capsule prepared by conventional techniques to contain the following

| Ingredient | Weight (mg.) |
| --- | --- |
| o-carbethoxyphenyl-n-propyl-n-octadecylsulfonium tetrafluoroborate | 25 to 1000 |
| Lactose | 250 |

Salts (the values ($Z^{\ominus}$) judged to be of particular interest generally include the tetrafluoroborate, perchlorate, methanesulfonate, phenylsulfonate and p-toluenesulfonate.

The following examples are illustrative of the invention. All temperatures are centigrade and room temperature is 20° to 30° C., unless indicated otherwise.

EXAMPLE 1 o-carbethoxyphenyl-n-propyl-n-octadecylsulfonium tetrafluoroborate

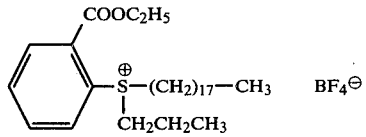

To a solution of 11.0 g n-octadecyl-ethyl thiosalicylate* and 4.25 g n-propyl iodide in 50 ml methylene chloride and 200 ml nitromethane is added 4.9 g silver tetrafluoroborate and the reaction mixture stirred at room temperature (under exclusion of light) for sixteen hours. The reaction mixture is then filtered free of solids and the filtrate evaporated under vacuum to dryness. The residue is dissolved in chloroform and chromatographed over silica gel with chloroform containing increasing concentrations of ethanol. The desired fractions are collected and evaporated under vacuum to dryness. From the residue is obtained on crystallization from ethanol the title compound m.p. 56°–58°. Upon repeated recrystallizations from diethyl ether, refined title product is obtained m.p. 60°–63°.
*may also be called 2-(n-octadecylthio) benzoic acid ethyl ester

EXAMPLE 2 p-(α-Carbethoxy)-tolyl-n-tetradecyl-phenylsulfonium tetrafluoroborate*

*may also be called (p-carbethoxymethyl)phenyl-n-tetradecyl-phenylsulfonium tetrafluoroborate

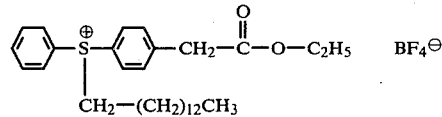

To a solution of 8.2 g p-carbethoxymethyldiphenylsulfide** and 9.7 g n-tetradecyl iodide in 100 ml nitromethane is added 5.8 g silver tetrafluoroborate. The reaction mixture is stirred at room temperature (under exclusion of light) for 16 hours. The reaction mixture is then filtered free of solids and the filtrate evaporated under vacuum to dryness. From the residue is crystallized from ethanol the title compound m.p. 36°–38°.

**may also be called 4-(phenylthio)phenylacetic acid ethyl ester, or p-(carbethoxymethyl)phenyl-phenyl sulfide

EXAMPLE 3 o-carboxyethoxyphenyl-n-propyl-n-octadecylsulfonium tetrafluoroborate

To a vessel equipped with a stirrer maintained under a dry nitrogen gas atmosphere, there is added 150 g of n-octadecyl-ethyl thio salicylicate, 105 ml of n-propyliodide and 3.0 L of toluene and stirred until dissolved. To the stirred solution is added, in one portion, 75 g of silver tetrafluoroborate. The reaction mixture is then stirred for 22 hours under the nitrogen atmosphere and protected from light. The resulting mixture is filtered through a Celite pad (50 g) to remove solids, which are then washed with 250 ml of toluene. The filtrate and wash are combined and evaporated (at 45°/20 mm) to obtain a residue. The residue is then dissolved in 1.5 L of diethyl ether, and the solution stirred at 5° for 18 hours, resulting in precipitation of the title product as a white solid (at lower temperatures unreacted starting material co-precipitates). The solid product is washed with 200 ml of cold diethylether, then dried (under vacuum at 25°/10 mm) to obtain refined title product, m.p. 60°–63°.

EXAMPLE 4

Repeating the procedure of Example 1, but using in place of the n-octadecyl-ethylthiosalicylate used therein, an approximately equivalent amount of:
(a) p-[2-(n-octadecylthio)]toluic acid ethyl ester
(b) m-[2-(n-octadecylthio)]toluic acid ethyl ester
(c) 5-chloro-2-(n-octadecylthio) benzoic acid ethyl ester
(d) 4-chloro-2-(n-octadecylthio) benzoic acid ethyl ester
(e) 3-methoxy-4-(n-octadecylthio) benzoic acid ethyl ester
(f) 3-methoxy-2-(n-octadecylthio) benzoic acid ethyl ester,
there is accordingly obtained:
(a) [(2-carbethoxy-5-methyl) phenyl]-(n-propyl)-(n-octadecyl) sulfonium tetrafluoroborate;
(b) [(2-carbethoxy-6-methyl)phenyl]-(n-propyl)-(n-octadecyl) sulfonium tetrafluoroborate;
(c) [(2-carbethoxy-4-chloro)phenyl]-(n-propyl)-n-octadecyl) sulfonium tetrafluoroborate;
(d) [(2-carbethoxy-5-chloro)-phenyl]-(n-propyl)-(n-octadecyl) sulfonium tetrafluoroborate;
(e) [(4-carbethoxy-2-methoxy)phenyl]-(n-propyl)-(n-octadecyl) sulfonium tetrafluoroborate; and
(f) [(2-carbethoxy-6-methoxy)phenyl]-(n-propyl)-(n-octadecyl) sulfonium tetrafluoroborate.

Repeating this example using the procedure of Example 3, likewise, yields products a) to f).

EXAMPLE 5

Following the procedure of Example 1 but using in place of the n-propyl iodide used therein, an approximately equivalent amount of
(a) n-butyl iodide;
(b) methyl iodide; or
(c) isopropyl iodide
there is accordingly obtained:
(a) o-carbethoxy phenyl-n-butyl-n-octadecylsulfonium tetrafluoroborate;
(b) o-carbethoxy phenyl-methyl-n-octadecylsulfonium tetrafluoroborate and (c) o-carbethoxy phenyl-isopropyl-n-octadecyl sulfonium tetrafluoroborate, m.p. 50°–52°.

Repeating this example using the procedure of Example 3, likewise yields products (a) to (c).

EXAMPLE 6

Repeating the procedure of Example 2, but using in place of the p-carbethoxymethyl-diphenylsulfide used therein, an approximately equivalent amount of:
(a) 4-carbethoxymethyl-3-chloro-diphenyl-sulfide;
(b) 4-carbethoxymethyl-3-methyl-diphenylsulfide;
(c) 4-carbethoxymethyl-3-methoxy-diphenylsulfide; or
(d) 4-carbethoxymethyl-3-methyl-4'-methyl diphenylsulfide;
there is accordingly obtained:
(a) [(3-chloro-4-carbethoxymethyl)phenyl]-n-tetradecylphenylsulfonium tetrafluoroborate;
(b) [4-carbethoxymethyl-3-methyl)phenyl]-n-tetradecylphenylsulfonium tetrafluoroborate;
(c) [4-carbethoxymethyl-3methoxy)phenyl]-n-tetradecylphenylsulfonium tetrafluoroborate; and
(d) [(4-carbethoxymethyl-3-methyl)phenyl]-n-tetradecyl-p-tolylsulfonium tetrafluoroborate.

EXAMPLE 7

Repeating the procedure of Example 2, but using in place of the n-tetadecyliodide used therein, an approximately equivalent amount of:
(a) n-dodecyliodide; or
(b) n-octadecyl iodide;
there is accordingly obtained:
(a) p-(α-carbethoxy)-tolyl-dodecyl-phenylsulfonium tetrafluoroborate; and
(b) p-(α-carbethoxy)-tolyl-n-octadecyl-phenylsulfonium tetrafluoroborate.

EXAMPLE 8 o-carbethoxyphenyl-n-propyl-n-octadecylsulfonium p-toluene sulfonate

To a solution of 5.0 g of o-carbethoxyphenyl-n-propyl-n-octadecylsulfonium tetrafluoroborate in 20 ml. of ethanol is added 20.0 g of potassium tosylate dissolved in a mixture of 200 ml. ethanol and 10 ml. water. The reaction mixture is maintained at 80°–90° while being stirred vigorously for 2 hours. The reaction mixture is then cooled and filtered, and the filtrate then evaporated under vacuum to dryness to obtain a residue. The residue is taken up in methylene chloride; the organic phase washed several times with water, dried over sodium sulphate, filtered and evaporated under vacuum to dryness. The residue is chromatographed over silica gel three times using methylene chloride and increasing amounts of methanol to obtain the title product m.p. 65°–67°.

EXAMPLE 9

Repeating the procedure of Example 7, but using in place of the potassium tosylate, an approximately equivalent amount of
(a) potassium bromide; or
(b) potassium trifluoromethylsulfonate;
there is accordingly obtained
(a) o-carbethoxyphenyl-n-propyl-n-octadecylsulfonium bromide; and
(b) o-carbethoxyphenyl-n-propyl-n-octadecylsulfonium trifluoromethylsulfonate.

EXAMPLE 10

Repeating the procedure of Example 1, but using an approximately equivalent amount of silver perchlorate in place of the silver tetrafluoroborate used therein, there accordingly is obtained o-carbethoxyphenyl-n-propyl-n-octadecylsulfonium perchlorate.

EXAMPLE 11 o-Carbethoxyphenyl-ethyl-n-octadecylsulfonium tetrafluoroborate

To a suspension of 2.0 g n-octadecylthiosalicylic acid in 150 ml methylene chloride is added excess of freshly prepared triethyloxonium tetrafluoroborate. The reaction mixture is stirred at room temperature for 48 hours. Thereafter methylenechloride layer is washed extensively with water, dried over anh. sodium sulfate, filtered and evaporated i.v. to dryness. The crude residue is then chromatographed over silica gel: eluting first with methylene chloride and then with methylene chloride containing increasing amounts of methanol. The desired fractions are collected and evaporated i.v. to give the title product.

EXAMPLE 12

Test A

Using as test compound o-carboxyphenyl-n-propyl-n-octadecylsulfonium tetrafluoroborate, in rats in the glucose transport test described above, an $E.D._{50}$ of 4.3 mg/kg is obtained.

Test B

In another test four male fasted Cebus monkeys (2.0–2.3 kg in body weight) are administered with the same compound in gelatin capsules at a dose level of 0 to 100 mg/kg animal body weight p.o.. One hour later, an oral glucose load (3.5 g/7 ml/kg) is given and then the blood sugar level is determined 30, 45, 60, 90, 120, 180 and 240 minutes thereafter as described above in balanced cross-over and latin square design to obtain glucose tolerance curves. The effective dose in lowering oral glucose tolerance curves is found to be about 100 mg/kg or slightly less for o-carbethoxyphenyl-n-propyl n-octadecylsulfonium tetrafluoroborate (title compound of Examples 1 and 3).

What is claimed is:

1. A compound of the formula:

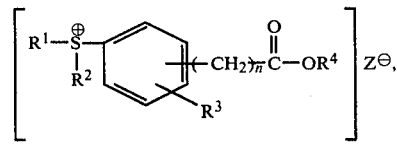

wherein
$R^1$ is alkyl having from 8 to 24 carbon atoms;
$R^2$ is alkyl having from 1 to 6 carbon atoms or unsubstituted or substituted phenyl of the formula:

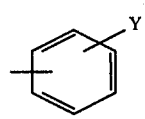

wherein

Y is a hydrogen atom, halo having an atomic weight of from about 19 to 80, alkyl of from 1 to 4 carbon atoms, or alkoxy of from 1 to 4 carbon atoms;

$R^3$ is a hydrogen atom, halo having an atomic weight of from about 19 to 80, alkyl having from 1 to 3 carbon atoms or alkoxy having from 1 to 3 carbon atoms;

$R^4$ is a hydrogen atom, or alkyl having from 1 to 6 carbon atoms;

n is 0 or 1; and $Z^{\ominus}$ is an anion forming a pharmaceutically acceptable non-toxic salt of the corresponding cation;

provided that $R^4$ is alkyl when $R^2$ is other than alkyl.

2. A compound of claim 1 in which Z is tetrafluoroborate.

3. A compound of claim 1 in which $R^4$ is alkyl.

4. A compound of claim 1 in which $R^2$ is alkyl.

5. A compound of claim 1 in which n is 0.

6. A compound of claim 1 in which $R^2$ is unsubstituted or substituted phenyl.

7. A compound of claim 1 in which n is 1.

8. The compound of claim 1 which is o-carbethoxyphenyl-n-propyl-n-octadecylsulfonium tetrafluoroborate.

9. The compound of claim 1 which is o-carbethoxyphenyl-n-propyl-n-octadecylsulfonium p-toluenesulfonate.

10. The compound of claim 1 which is p-($\alpha$-carbethoxy)-tolyl-n-tetradecyl-phenylsulfonium tetrafluoroborate.

11. A compound of inhibiting or retarding the passage of glucose into the blood in a mammal, comprising administering to a mammal an amount of a compound of claim 1, effective in inhibiting or retarding the passage of glucose into the blood of the mammal.

12. A method of claim 11 in which $R^1$ is alkyl having from 10 to 20 carbon atoms.

13. A method of claim 11 in which the compound is administered in a solid form.

14. A method of claim 13 in which the compound is o-carbethoxyphenyl-n-propyl-n-octadecylsulfonium tetrafluoroborate.

15. A composition comprising in a unit dosage form a pharmaceutically acceptable carrier and from about 25 to 1000 milligrams of a compound as defined in claim 1.

16. A composition of claim 15 in which $R^1$ of the compound is alkyl having from 10 to 20 carbon atoms.

17. A composition of claim 15 in which the carrier is solid.

18. A composition of claim 15 in which the compound is o-carbethoxyphenyl-n-propyl-n-octadecylsulfonium tetrafluoroborate.

19. A composition of claim 15 which is in the form of a tablet or hard-filled capsule.

20. The compound of claim 1 which is o-carbethoxyphenyl-isopropyl-n-octadecylsulfonium tetrafluoroborate.

21. A method of claim 11 in which the compound is administered at from about 60 to 3600 milligrams per day.

22. The method of claims 11 or 21 in which the compound is o-carbethoxyphenyl-n-propyl-octadecylsulfonium tetrafluoroborate.

23. A pharmaceutical composition comprising an amount of a compound of claim 1 effective in inhibiting or retarding the passage of glucose into the blood of said mammal and a non-toxic pharmaceutically-acceptable carrier.

24. A composition of claim 23 in which the compound is o-carbethoxyphenyl-n-propyl-octadecylsulfonium tetrafluoroborate.

25. A composition of claim 23 in which the compound is present in an amount of from about 15 to 1200 milligrams.

26. A method of claim 11 in which post-prandial hyperglycemia is treated in a diabetic subject.

27. A method of claim 11 in which obesity is treated.

* * * * *